(12) United States Patent
Sathish et al.

(10) Patent No.: US 7,918,141 B1
(45) Date of Patent: Apr. 5, 2011

(54) LOCAL RESIDUAL STRESS MEASUREMENT AND ANALYSIS FOR DETECTION AND PREDICTION OF DAMAGE IN THERMAL BARRIER COATINGS

(75) Inventors: Shamachary Sathish, Bellbrook, OH (US); Sonia A. Martinez, Ellington, CT (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 11/973,977

(22) Filed: Oct. 4, 2007

Related U.S. Application Data

(60) Provisional application No. 60/909,823, filed on Apr. 3, 2007.

(51) Int. Cl.
*G01L 5/00* (2006.01)

(52) U.S. Cl. .......................................... 73/800; 73/105

(58) Field of Classification Search .................... 73/105, 73/800; 250/307; 324/637; 356/32
See application file for complete search history.

(56) References Cited

U.S. PATENT DOCUMENTS

| | | | | |
|---|---|---|---|---|
| 4,806,849 | A * | 2/1989 | Kihira et al. | 324/700 |
| 5,015,950 | A * | 5/1991 | Rose et al. | 324/224 |
| 5,490,426 | A | 2/1996 | Shiga et al. | |
| 5,817,945 | A * | 10/1998 | Morris et al. | 73/800 |
| 5,847,283 | A * | 12/1998 | Finot et al. | 73/812 |
| 6,072,568 | A | 6/2000 | Paton et al. | |
| 6,221,512 | B1 | 4/2001 | Rickerby | |
| 6,240,784 | B1 * | 6/2001 | Koike et al. | 73/597 |
| 6,968,730 | B2 | 11/2005 | Schafrik et al. | |
| 6,979,991 | B2 * | 12/2005 | Burns et al. | 324/71.1 |
| 7,250,776 | B2 * | 7/2007 | Twerdochlib | 324/693 |
| 7,334,330 | B2 * | 2/2008 | Vance | 29/889.2 |
| 2003/0193331 | A1 * | 10/2003 | Nath et al. | 324/240 |
| 2004/0082069 | A1 * | 4/2004 | Jiang et al. | 436/2 |
| 2006/0216534 | A1 * | 9/2006 | Boutwell et al. | 428/472 |
| 2007/0217672 | A1 * | 9/2007 | Shannon et al. | 382/152 |

\* cited by examiner

*Primary Examiner* — Freddie Kirkland, III
(74) *Attorney, Agent, or Firm* — AFMCLO/JAZ; James P. Calve

(57) ABSTRACT

The present invention provides a method for evaluating degradation of a thermal barrier coating disposed on a turbine blade. The method includes measuring a residual stress of an outer surface portion of a thermal barrier coating on a turbine blade, the turbine blade having been subjected to normal operating conditions and determining degradation of the thermal barrier coating based on a comparison between the residual stress measurement and a control stress measurement.

20 Claims, 3 Drawing Sheets

LOCAL RESIDUAL STRESS MEASUREMENT AND ANALYSIS FOR DETECTION AND PREDICTION OF DAMAGE IN THERMAL BARRIER COATINGS

CROSS-REFERENCE TO RELATED APPLICATIONS

This application is related to and claims priority from co-pending U.S. Provisional Patent Application No. 60/909,823, filed on Apr. 3, 2007 and entitled "Local Residual Stress Measurement and Analysis for Detection and Prediction of Damage in Thermal Barrier Coatings."

RIGHTS OF THE GOVERNMENT

The invention described herein may be manufactured and used by or for the Government of the United States for all governmental purposes without the payment of any royalty.

BACKGROUND OF THE INVENTION

The present invention relates to a methodology for detecting and predicting damage in thermal barrier coatings. Thermal Barrier Coatings (TBC's) are widely used in high temperature sections of aerospace engines and thermal power generators. More specifically, the barrier coatings are applied to turbine blades and other critical components of engines and generators to provide insulation from very high temperatures. With the application of the barrier coating, components can be used at temperatures very close to or higher than their melting point temperature.

One common method of applying thermal barrier coatings is by plasma spraying. Other methods include, for example, Physical vapor deposition (PVD) and Electron Beam Physical Vapor Deposition (EBPVD). Usually, the coating consists of a layer of partially stabilized zirconia, over an oxidation-resistant metallic bond coat of MCrAlY that is deposited on a substrate, where typically M is Ni and/or Co. During the life cycle of an engine or generator, the coatings degrade due to excess temperature and mechanical stresses. This degradation causes the TBC to peel off from the substrate thereby exposing the substrate to very high temperatures. Exposure of extreme temperatures to a TBC-free substrate could cause catastrophic engine and generator failures.

Various non-destructive evaluation methods are available for characterizing thermal barrier coatings. Conventional NDE methods include visual inspection, thermography, eddy current, microwave and ultrasonics. Optical NDE methods include laser backscatter, optical coherence tomography, mid infrared backscatter, and luminescence based piezospectroscopy. Most of these NDE techniques often detect surface condition and delamination between substrate and the barrier coating. Luminescence based piezospectroscopy detects stress changes in bond coating.

U.S. Pat. No. 6,968,730 to Schafrik et al. discloses a non-destructive method of detecting subsurface defects in thermal barrier coatings applied to gas turbine engine components. In an exemplary embodiment, the method includes positioning a evanescent microwave microscope probe adjacent a turbine component surface coated with a thermal barrier coating, and scanning the thermal barrier coating by moving at least one of the evanescent microwave microscope probe and the component surface in relation to one another in an x-y plane while maintaining a predetermined distance between the probe and the thermal barrier coating constant. In the background section of the Schafrik et al. patent, it is stated that standard non-destructive testing techniques, for example, through transmission ultrasound and X-ray diffraction may be unable to assess thermal barrier coating integrity due to density differences between the substrate and the coating. Known residual stress measurement techniques, such as X-ray diffraction, have limited use in determining thermal barrier coating quality because of the difficulty in penetrating through the thermal insulating layer to the intermediate layer.

U.S. Pat. No. 6,072,568 to Paton et al. discloses a non-destructive measurement method for determining residual stress proximate an intermediate layer in a multilayer thermal barrier coating system by directing a laser beam through an outer ceramic thermal insulating layer with the laser beam illuminating a ceramic-bearing intermediate layer in a manner to cause species present in the intermediate layer to fluoresce, measuring the frequency of the light or photons emitted by the fluroescing species, and comparing the measured frequency shift of the intermediate ceramic layer to the frequency shift determined on like ceramic material under controlled stress states to determine a representation of relative residual stress in the measured coating. The invention can be used to assess integrity or quality control of as-manufactured TBC coatings or to assess remaining coating service life of engine-run TBC coated components during an inspection or repair procedure. The background section of the Paton et al. patent states that residual stress measurement techniques such as X-ray diffraction have been of limited use in determining residual compressive stress of TBC systems due in large part to the difficulty in penetrating through the thermal insulating layer to the intermediate layer. The intermediate layer also is very thin (e.g. 1 micron thickness) and is therefore very difficult to characterize by X-ray diffraction and other conventional techniques such as neutron diffraction.

Also, U.S. Pat. No. 5,490,426 to Shiga et al. teaches a method for detecting stresses which includes the steps of dispersing a fluorescent substance in a solid portion where stresses are to be detected, measuring fluorescence decay time of the fluorescent substance dispersed in the solid portion, and detecting stresses in the solid portion based on the measured fluorescence decay time. The method enables to non-destructively detect stresses in resin-molded products without impairing their mechanical properties.

Luminescence based piezospectroscopy, described in U.S. Pat. No. 6,072,568 to Paton et al. and U.S. Pat. No. 5,490,426 to Shiga et al., is a spectroscopic technique based on laser interaction with the material. The laser based technique has limited application when the optical transparency of the TBC is reduced due to usage. Recently, spectroscopic techniques have been developed to assess the health of thermal barrier coatings. These techniques attempt to evaluate the bond coat between the substrate and the coating. Since the radiation has to pass through the barrier coating, scattering and absorption by the coating limits the applicability of the optical techniques.

Therefore, there is a need for a non-destructive evaluation technique that can provide information about the rate of degradation of thermal barrier coatings and that can provide information to detect and predict the failure of the coatings.

SUMMARY OF THE INVENTION

The present invention provides a methodology for detecting and predicting damage in thermal barrier coatings applied to a substrate such as an engine turbine blade.

In accordance with one aspect of the invention, there is provided a method for evaluating degradation of a thermal barrier coating disposed on a turbine blade. The method includes measuring residual stress of an outer surface portion of a thermal barrier coating on a turbine blade. The turbine blade is one that has been subjected to normal operating conditions. The method also includes determining degradation of the thermal barrier coating based on a comparison between the residual stress measurement and a control sample stress measurement. The control sample may be a separate substrate that was coated during processing of the TBC, or the control sample may be a region on the turbine blade that was not exposed to the harshest operating environment. For example, the control sample may be the root of the blade which is cooler than the leading edge of the blade and cooler, for that matter, than the entire body portion of the blade.

The control stress measurement may be approximately zero. This control zero stress is the final stress. That is, a control stress measurement of zero indicates that point in the barrier coatings service life in which the coating has delaminated from the substrate or the coating is likely to delaminate from the substrate. In such a case, the method may further include removing the turbine blade from operational use when the residual stress measurement is approximately equal to the zero. Alternatively, the control stress measurement may be a predetermined minimum residual stress safety level. The predetermined minimum residual stress safety level being greater than zero. In this situation, the method may include removing the turbine blade from operational use when the residual stress measurement is approximately equal to the predetermined minimum residual stress safety level.

In accordance with another aspect of the invention, there is provided a method for evaluating degradation of a thermal barrier coating disposed on a turbine blade. The method includes measuring a residual stress of a barrier coating on a first turbine blade. The first turbine blade is one that has not been subjected to normal operating temperatures. The method also includes measuring a residual stress of a barrier coating on a second turbine blade. The second turbine blade is one that has been subjected to normal operating temperatures. Furthermore, the method includes comparing the residual stress measurements taken from the first and second turbine blades and determining degradation of the thermal barrier coating of the second turbine blade based on the comparison of the residual stress measurements.

In a related aspect of the invention, the thermal barrier coating may include a crystalline material. Measuring the residual stress may be performed with x-ray diffraction. The x-ray radiation may penetrate the barrier coating up to about 5 μm-10 μm. Measuring the residual stress may also be performed with other methods such as neutron diffraction, ultrasound, or optical spectroscopic techniques.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE INVENTION

The present invention provides a technique for detecting the degradation of thermal barrier coatings applied to a substrate, such as a turbine engine blade, and predicting the failure of the barrier coating. The principle of measuring and predicting degradation of thermal barrier coatings is through observing the changes in surface residual stresses. The TBC degrades when oxygen in the atmosphere diffuses through the coating and attacks the bond coat at the substrate. The oxygen reacts with the aluminum (Al) of the coating material, MCrAlY, and oxidizes it. Whenever the process of oxidation depletes the aluminum content in the bond coat, the local residual stress in the vicinity of the oxidized region is altered. This produces local residual stress changes at the top surface or near top surface of the TBC. When complete delamination occurs at the bond coat substrate interface, the compressive residual stress at the top surface or outer surface portion of the TBC reaches zero. Any further use of the turbine blade will result in peeling off of the TBC, causing damage to the engine or generator.

Figure 1:
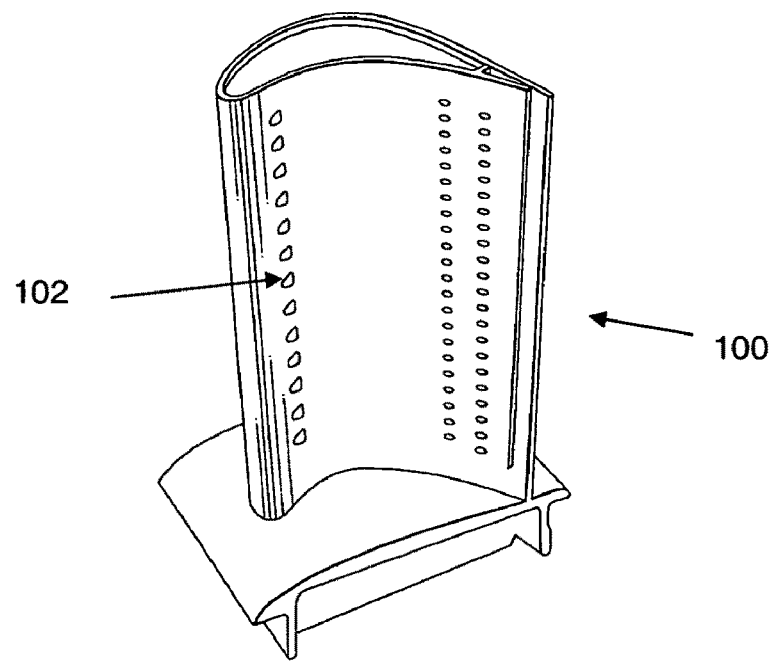
FIG. 1 is a perspective view of a turbine blade.
Figure 1A:
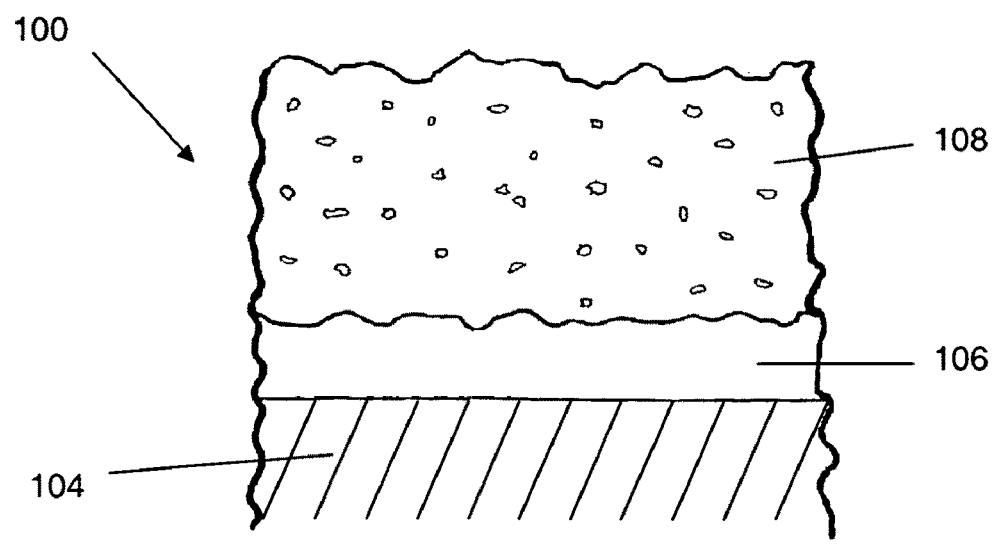
FIG. 1a is a cross sectional view of a blade with a thermal barrier coating.

Referring now to the drawings, FIG. 1 illustrates a typical turbine blade 100. During operation of the engine, the turbine blade is subjected to extreme temperatures. The thermal barrier coating applied to the blade, as well as various cooling holes 102, help protect the blade material from being damaged and destroyed. Failure of turbine blade, of course, can lead to catastrophic failure of the engine. In FIG. 1a, a cross section view of a typical turbine blade 100 is shown. The body 104 of the blade 100 is usually made of a superalloy or may be made from composite materials. An intermediate layer 106 is disposed on the blade 100. The intermediate layer 106 may be, for example, an oxidation-resistant bond coat. The insulative layer 108 is disposed on the intermediate layer 106. The insulative layer 108 may be, for example, Yttria-stabilized zirconia.

One method for measuring stress is x-ray diffraction. Generally, in x-ray diffraction stress measurements, changes in inter-planar spacing (strain) due to an external or residual stress are determined. The stress responsible for strain is evaluated assuming linear elastic deformation of the material. When x-rays are incident on a polycrystalline material, diffraction occurs from crystallographic planes, whenever the Bragg's Law: $n\lambda = 2d \sin \theta$, is satisfied. Here, n is an integer representing the order of diffraction (typically 1), λ is the x-ray wavelength, d is the interplanar spacing of crystal planes (hkl), and θ is the diffraction angle.

For an isotropic polycrystalline material as in the case of TBC, the strain can be related to the stress by combining the Bragg's Law with the Hooke's Law.

$$\frac{d_{\varphi\psi} - d_0}{d_0} = \frac{1+\upsilon}{E} \sigma_\varphi \sin^2 \psi \qquad \text{Equation (1)}$$

$$\sigma_\phi = \sigma_{11} \cos^2 \phi + \sigma_{22} \sin^2 \phi \qquad \text{Equation (2)}$$

In the above equations, $(d_{\varphi\psi} - d_0)/d_0$ represents the strain obtained from the position of the diffraction peak for a given reflection, hkl, acting perpendicular to the free surface; $d_0$ is the unstressed lattice spacing at $\psi = 0$; and $d_{\varphi\psi}$ is the lattice spacing obtained from the position of the diffraction peak for a crystallographic plane (hkl) in the direction $\phi, \psi$ tilt. $S_1 = $ v/E and $S_2=(1+v)/E$ are x-ray elastic constants, where E is the Young's modulus and v is the Poisson's ratio of the material. $\sigma_\phi$ is the biaxial stress tensor. Experimentally, to determine the residual stress, the strain is measured at different angles of ψ and a plot of d versus $\sin^2$ ψ is obtained. Using the slope of the curve and the x-ray elastic constants in Equation (1), the residual stress is determined.

In the measurements of the present invention, an x-ray diffraction residual stress analyzer with horizontal goniometer fixture was utilized. Copper K-alpha radiation collimated to a diameter of 1-2 mm was employed. The penetration of x-ray radiation is about 5 μm into the surface of the coating. Therefore, the strain measured will be close to the top insulating layer (zirconia layer) and will not represent the strain within the bulk of the coating. Diffraction from the (620) crystallographic plane of the $ZrO_2$ was selected for measurement. The diffraction angle for this plane was 2θ=144.5°. The Young modulus for the plane was E=22 GPa and v=0.23 and were used in order to calculate the residual stress from Equation (1).

Nickel filters were utilized to reduce the intensity of copper K-β radiation. Two detectors were utilized in this set-up covering both ψ+ and ψ−. An oscillation of 5 degrees around the mean position of the goniometer was used in order to enhance the signal to noise ratio. After collecting the diffraction peak data, a Gaussian peak fitting algorithm was used to fit and determine the center of the diffraction peak. Lorentz Polarization and absorption corrections were applied to raw intensity data. The d spacing was determined at 9 different angles. The residual stress at a location was determined using Equation (1).

In addition to x-ray diffraction, other methods may be used to measure residual stress in a thermal barrier coating. Such methods include neutron diffraction, ultrasonic velocity measurements, and optical spectroscopic methods measuring shift in the spectral lines. For the present invention, the use of x-ray diffraction is used for thermal barrier coatings having crystalline materials.

In one exemplary embodiment, degradation of a thermal barrier coating may be determined by measuring the residual stress of the barrier coating applied to a turbine blade that has been exposed to operating conditions. That is, the blade was used in a turbine engine or generator and was subjected to temperatures, pressures, strains, and vibrations during normal operation of the engine or generator. X-ray diffraction, neutron diffraction, ultrasound, or optical spectroscopic methods may be used to measure the residual stress. The residual stress of the outer portion of the thermal barrier coating need be measured. For example, when using x-ray diffraction, the x-ray radiation penetrates about 5 μm into the coating.

As stated in the prior art, residual stress measurement techniques such as X-ray diffraction have been of limited use in determining residual compressive stress of TBC systems due in large part to the difficulty in penetrating through the thermal insulating layer to the intermediate layer. The present invention overcomes this problem by measuring residual stress of the thermal insulating layer only.

After the residual stress of the insulating layer of the TBC is measured, this amount may be compared to the residual stress of a delaminated TBC. Typically, the residual stress of a delaminated TBC is zero. Therefore, if the measured residual stress is zero or is approaching zero, the TBC may be delaminated or close to delaminating from the blade, even though the TBC does not appear to be delaminated upon visual inspection. At this point, the blade may be removed from service and repaired or discarded.

In another exemplary embodiment, degradation of a thermal barrier coating may be determined by measuring the residual stress of the barrier coating applied to a turbine blade that has been exposed to operating temperatures, pressures, strains, and vibrations. Again, x-ray diffraction, neutron diffraction, or ultrasound may be used to measure the residual stress. The residual stress of the upper surface portion of the thermal barrier coating need be measured. For example, when using x-ray diffraction, the x-ray radiation penetrates about 5 μm into the coating. After the residual stress of the insulating layer of the TBC is measured, this amount may be compared to a predetermined minimum residual stress safety level. If the measured residual stress is at or is close to the predetermined minimum residual stress safety level, then the TBC may be close to delaminating from the blade.

In yet another embodiment of the invention, degradation of a thermal barrier coating may be determined by comparing residual stress of a "used" turbine blade to a "new" turbine blade. The residual stress of a TBC applied to a turbine blade that has been exposed to operating conditions (used) is measured using x-ray diffraction or another suitable method. The residual stress of a TBC applied to a turbine blade that has not been subjected to operating conditions (new) is measured. The residual stress measurements are compared to determine the amount of degradation of the used TBC relative to the new TBC. Based on the number of operating hours on the used turbine blade and the measured residual, stress, the remaining life cycle of the TBC on the used blade may be calculated. That is, for example, if the residual stress of the TBC on the new blade is 300 MPa, the residual stress of the TBC on the used blade is 200 MPa, the number of operating hours on the used blade is 500, then in approximately 1,000 hours of continued operation, the TBC on the used blade will be close to failing or delaminating.

Figure 2:
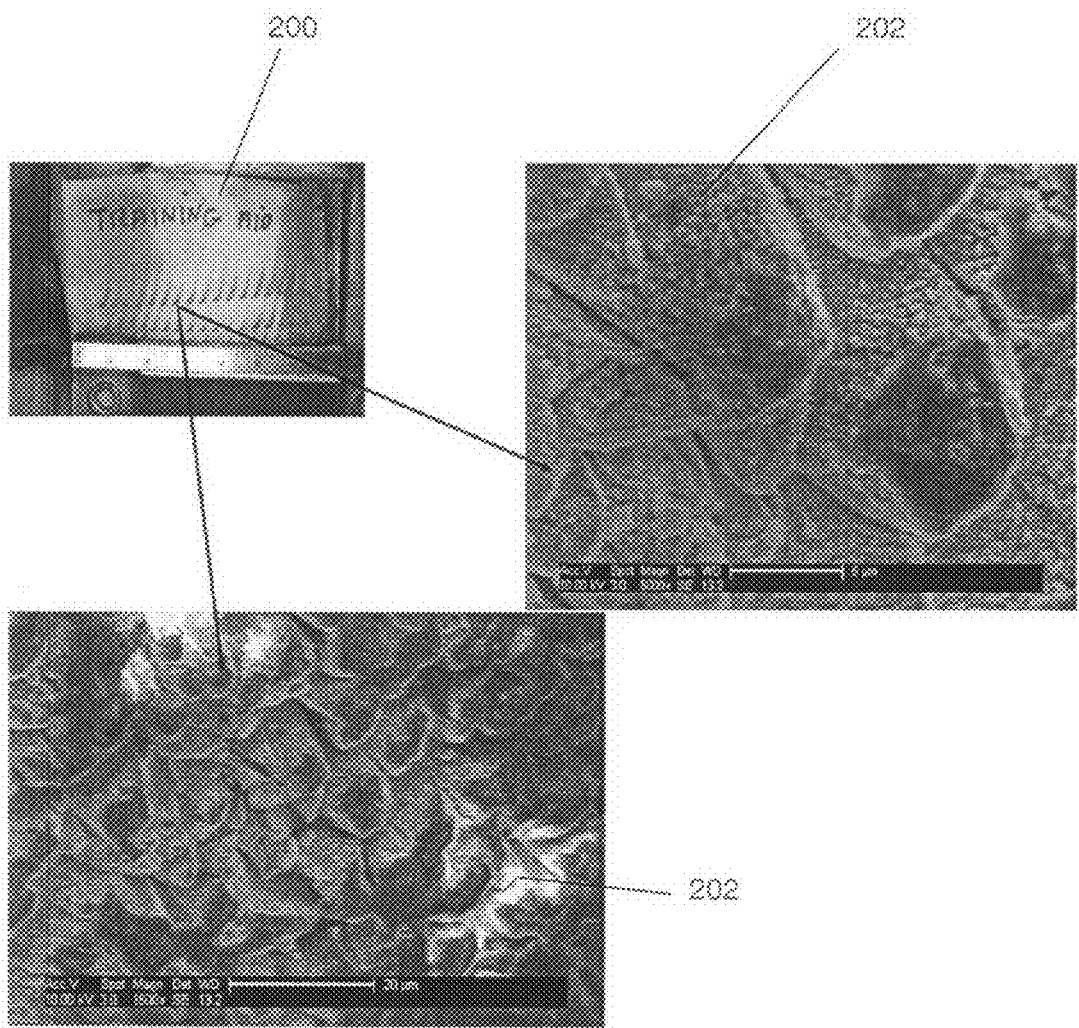
FIG. 2 is an optical photograph and SEM images with higher magnification showing the microstructure of the TBC of a retired turbine blade.

In an experiment to prove the present invention, the methodology measurements were performed on a turbine blade discarded from service. This blade 200 is illustrated in FIG. 2. The blade 200 endured the actual harsh environment of an aerospace engine. There are regions where the TBC is intact while in other locations, the barrier coating 202 is spalling. Particularly in regions of the leading edge, the TBC 202 peeled off and in some regions the TBC is about to peel off. Measurements of residual stress were performed in many regions to observe variations.

The parameters used for the measurement of residual stress were as follows. X-ray diffraction radiation was Copper Kα (0.154 nm) with Ni filter. Operating conditions were 22 kV/4 mA. Diameter of the x-ray spot was 1 mm. Lattice planes for analysis reflection from (hkl) was [620] of $ZrO_2$.

Figure 3:
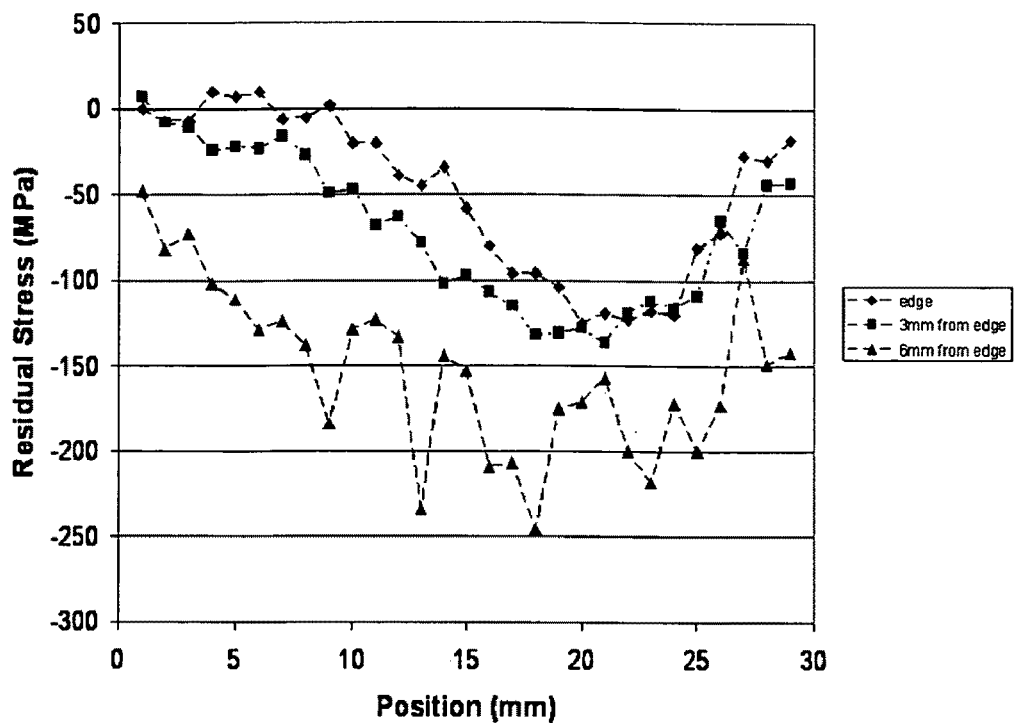
FIG. 3 is a graph showing residual stress measurements of a convex surface of the blade of FIG. 2, at different distances from the leading edge.

FIG. 3 shows the residual stress at different positions from the leading edge of the turbine blade on the convex side of the blade. The x-axis of the chart of FIG. 3 is the position from the root of the blade moving out to the tip of the blade. The residual stress at the leading edge is somewhat higher than 3 mm from the edge and 6 mm from the edge. The residual stress is least at a location 6 mm from the leading edge and 10 mm to 25 mm along the length of the blade. This low stress region coincides with a discoloration area on the blade. The average stress of this region was −258+/−42 MPa.

Figure 4:
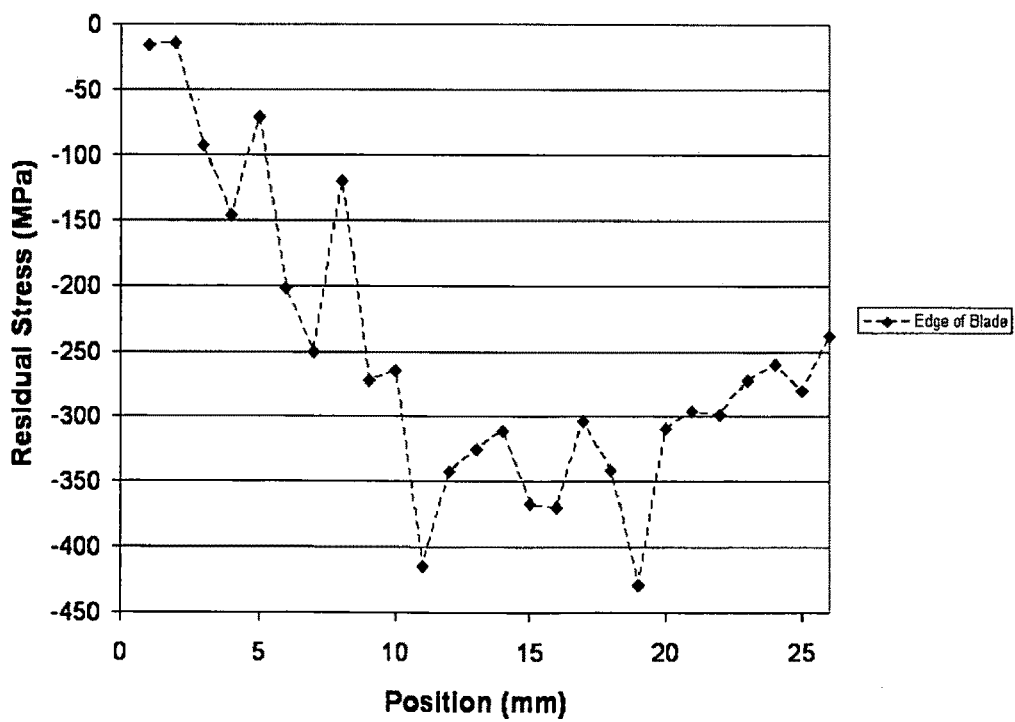
FIG. 4 is a graph showing residual stress measurements of a concave surface of the blade of FIG. 2, near the leading edge of the blade.

FIG. 4 shows the residual stress at the leading edge of the turbine blade on the concave side of the blade. Like the chart of FIG. 3, the x-axis of the chart of FIG. 4 is the position from the root of the blade moving out to the tip of the blade. The residual stress is least at a location along the leading edge and 11 mm to 22 mm along the length of the blade. This low stress region coincides with a discoloration area on the blade. The average stress of this region was −113+/−35 MPa.

The average residual stress in TBC intact regions was >−300+/−40 MPa. The average residual stress in TBC discolored regions was <−100+/−35 MPa. There was complete relaxation (0 MPa) of residual stress in the vicinity of delaminated regions.

The residual stress in the regions that appear to be intact was highly compressive, while in regions while in regions that appear to have discoloration were lower in residual stress. In regions where the TBC is peeling off, especially close to the leading edge, the compressive residual stress had almost disappeared. These measurements indicate that the healthy region of the TBC has high compressive residual stress and as the coating degrades the residual stress decreases. When the compressive residual stress approaches zero or becomes zero, the barrier coating peels away from or off from the blade.

X-ray diffraction residual stress measurements were performed around a cooling hole. Measurements were performed with x-ray spot size of 1 mm. The sample was moved in the x and y directions with a step size of 0.25 mm, and the data was collected at each and every location.

There is significant variation in the residual stress around the cooling hole. The low compressive residual stress side is the direction in which the cooling gases have emerged out. The gas coming out is quite hot, and hence the residual stress has decreased compared to the other side.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for evaluating degradation of a thermal barrier coating disposed on a turbine blade, the method comprising:
   measuring a residual stress at an outermost layer of a thermal barrier coating on a turbine blade by penetrating radiation up to about 10 μm into the outermost layer, the turbine blade having been subjected to normal operating conditions; and
   determining degradation of the thermal barrier coating based on a comparison between the residual stress measurement and a control stress measurement.

2. The method of claim 1 wherein the control stress measurement is approximately zero.

3. The method of claim 2 further including removing the turbine blade from operational use when the residual stress measurement is approximately equal to zero.

4. The method of claim 1 wherein the control stress measurement is a predetermined minimum residual stress safety level, the predetermined minimum residual stress safety level being greater than zero.

5. The method of claim 4 further including removing the turbine blade from operational use when the residual stress measurement is approximately equal to the predetermined minimum residual stress safety level.

6. The method of claim 1 wherein the thermal barrier coating is crystalline.

7. The method of claim 6 wherein measuring the residual stress is performed with x-ray diffraction.

8. The method of claim 7 wherein x-ray radiation penetrates the barrier coating up to about 5 μm.

9. The method of claim 1 wherein measuring the residual stress is performed with neutron diffraction.

10. The method of claim 1 wherein measuring the residual stress is performed with ultrasound.

11. The method of claim 1, wherein the outermost layer is penetrated by x-ray, neutron, ultrasonic, or optical spectroscopic radiation about 5 μm to about 10 μm.

12. The method of claim 1, wherein measuring the residual stress is performed with optical spectroscopic techniques.

13. A method for evaluating degradation of a thermal barrier coating disposed on a turbine blade, the method comprising:
   measuring a residual stress at an outermost layer of a barrier coating on a first turbine blade by penetrating radiation up to about 10 μm into the outermost layer, the first turbine blade not having been subjected to normal operating temperatures;
   measuring a residual stress of an outermost insulative layer of a barrier coating on a second turbine blade by penetrating radiation up to about 10 μm into the outermost layer, the second turbine blade having been subjected to normal operating temperatures;
   comparing the residual stress measurements taken from the first and second turbine blades; and
   determining degradation of the thermal barrier coating of the second turbine blade based on the comparison of the residual stress measurements.

14. The method of claim 13 wherein the thermal barrier coatings are crystalline.

15. The method of claim 14 wherein measuring the residual stress is performed with x-ray diffraction.

16. The method of claim 15 wherein x-ray radiation penetrates the barrier coating up to about 5 μm.

17. The method of claim 13 wherein measuring the residual stress is performed with neutron diffraction.

18. The method of claim 13 wherein measuring the residual stress is performed with ultrasound.

19. The method of claim 13, wherein the outermost layer is penetrated by x-ray, neutron, ultrasonic, or optical spectroscopic radiation about 5 μm to about 10 μm.

20. The method of claim 13, wherein measuring the residual stress is performed with optical spectroscopic techniques.

* * * * *